US008574899B2

(12) United States Patent
Serikov et al.

(10) Patent No.: US 8,574,899 B2
(45) Date of Patent: Nov. 5, 2013

(54) METHODS FOR AUGMENTATION COLLECTION OF PLACENTAL HEMATOPOIETIC STEM CELLS AND USES THEREOF

(76) Inventors: Vladimir B Serikov, Martinez, CA (US); Frans A Kuypers, El Cerrito, CA (US)

( * ) Notice: Subject to any disclaimer, the term of this patent is extended or adjusted under 35 U.S.C. 154(b) by 0 days.

(21) Appl. No.: 13/374,105

(22) Filed: Dec. 12, 2011

(65) Prior Publication Data

US 2012/0177616 A1 Jul. 12, 2012

Related U.S. Application Data

(60) Provisional application No. 61/459,922, filed on Dec. 22, 2010.

(51) Int. Cl.
*C12N 5/00* (2006.01)

(52) U.S. Cl.
USPC .......... 435/325; 435/372; 435/378; 424/93.7

(58) Field of Classification Search
None
See application file for complete search history.

(56) References Cited

U.S. PATENT DOCUMENTS

| | | | |
|---|---|---|---|
| 3,862,002 A | 1/1975 | Sanders | |
| 5,372,581 A | 12/1994 | Anderson | |
| 5,415,665 A | 5/1995 | Hessel et al. | |
| 5,643,741 A | 7/1997 | Tsukamoto et al. | |
| 5,912,266 A | 6/1999 | Perez | |
| 6,059,968 A | 5/2000 | Wolf, Jr. | |
| 6,179,819 B1 | 1/2001 | Haswell | |
| 6,338,942 B2 | 1/2002 | Kraus et al. | |
| 6,849,639 B2 | 2/2005 | Dominguez et al. | |
| 7,045,148 B2 | 5/2006 | Hariri | |
| 7,147,626 B2 | 12/2006 | Goodman et al. | |
| 7,255,879 B2 | 8/2007 | Hariri | |
| 7,311,905 B2 | 12/2007 | Hariri | |
| 7,399,632 B2 | 7/2008 | Simmons et al. | |
| 7,413,734 B2 | 8/2008 | Mistry et al. | |
| 7,468,276 B2 | 12/2008 | Hariri | |

(Continued)

FOREIGN PATENT DOCUMENTS

WO WO-0110841 2/2001
WO WO-2005001080 1/2005

(Continued)

OTHER PUBLICATIONS

Serikov et al., Exper. Biol. Medic., 234:813-823 (2009).*
Bailo et al. "Engraftment Potential of Human Amnion and Chorion Cells Derived from Term Placenta," *Transplantation*, vol. 78, 2004, pp. 1439-1448.

(Continued)

*Primary Examiner* — Blaine Lankford
*Assistant Examiner* — Thomas J Visone
(74) *Attorney, Agent, or Firm* — Goodwin Procter LLP

(57) ABSTRACT

The subject matter of this invention is a novel method to augment the process of obtaining populations of placental hematopoietic stem and progenitor cells for use in medical practices. A method of augmentation of stem cells collection from placenta is claimed comprising the steps of (a) infusing placental vessels cell preservation compound and a with a composition containing blockers of cell adhesion receptors, (b) incubating said placenta for a sufficient period of time, (c) placing placenta in a containment with sufficient intensity of electromagnetic or ultrasound field for a sufficient period of time; (d) eluting cell suspension from placental vessels, (e) collecting cell suspension and harvesting cells. Invention further claims a method of treatment a disease by means of administering therapeutic composition containing said placental-derived hematopoietic stem cells.

14 Claims, 1 Drawing Sheet

(56) References Cited

U.S. PATENT DOCUMENTS

| | | |
|---|---|---|
| 7,498,171 B2 | 3/2009 | Hariri et al. |
| 7,510,873 B2 | 3/2009 | Mistry et al. |
| 7,524,489 B2 | 4/2009 | Messina et al. |
| 7,534,606 B2 | 5/2009 | Chen et al. |
| 7,547,564 B2 | 6/2009 | Lee et al. |
| 7,560,276 B2 | 7/2009 | Harmon et al. |
| 7,601,114 B2 | 10/2009 | Goodwin et al. |
| 2003/0235563 A1 | 12/2003 | Strom et al. |
| 2004/0048372 A1 | 3/2004 | Hariri |
| 2004/0107453 A1 | 6/2004 | Furcht et al. |
| 2004/0136967 A1 | 7/2004 | Weiss et al. |
| 2004/0161419 A1 | 8/2004 | Strom et al. |
| 2005/0054093 A1 | 3/2005 | Haas |
| 2005/0124003 A1 | 6/2005 | Atala et al. |
| 2005/0176139 A1 | 8/2005 | Chen et al. |
| 2006/0154366 A1 | 7/2006 | Brown et al. |
| 2006/0154367 A1 | 7/2006 | Kihm et al. |
| 2006/0166361 A1 | 7/2006 | Seyda et al. |
| 2006/0171930 A1 | 8/2006 | Seyda et al. |
| 2006/0188983 A1 | 8/2006 | Harris et al. |
| 2006/0222634 A1 | 10/2006 | Clarke et al. |
| 2006/0233765 A1 | 10/2006 | Messina et al. |
| 2006/0233766 A1 | 10/2006 | Messina et al. |
| 2006/0234376 A1 | 10/2006 | Mistry et al. |
| 2006/0281178 A1 | 12/2006 | Sakuragawa et al. |
| 2007/0065420 A1 | 3/2007 | Johnson |
| 2007/0092497 A1 | 4/2007 | Hariri |
| 2007/0190034 A1 | 8/2007 | Paludan et al. |
| 2007/0190042 A1 | 8/2007 | Edinger et al. |
| 2007/0275362 A1 | 11/2007 | Edinger et al. |
| 2008/0032401 A1 | 2/2008 | Edinger et al. |
| 2008/0131410 A1 | 6/2008 | Hariri |
| 2010/0248206 A1 | 9/2010 | Kuypers |

FOREIGN PATENT DOCUMENTS

| | | |
|---|---|---|
| WO | WO-2005003334 | 1/2005 |
| WO | WO-2006071773 | 7/2006 |
| WO | WO-2006071777 | 7/2006 |
| WO | WO-2006071778 | 7/2006 |
| WO | WO-2006071794 | 7/2006 |
| WO | WO-2006071802 | 7/2006 |
| WO | WO-2008019148 | 2/2008 |
| WO | WO-2008100498 | 8/2008 |
| WO | WO-2008156659 | 12/2008 |

OTHER PUBLICATIONS

Cashen et al. "AMD3100: CXCR4 Antagonist and Rapid Stem Cell-Mobilizing Agent," *Future Oncolocy*, vol. 3(1), 2007, pp. 19-27 (abstract only).

Chien et al. "In Vitro Differentiation of Human Placenta-Derived Multipotent Cells into Hepatocyte-Like Cells," *Stem Cells*, 2006, vol. 24, pp. 1759-1768.

De Coppi et al. "Isolation of Amniotic Stem Cell Lines with Potential for Therapy," *Nature Biotechnology*, 2007, vol. 25, pp. 100-106.

Dominici et al. "Minimal Criteria for Defining Multipotent Mesenchymal Stem Cells," *Cytotherapy*, 2006, vol. 8, pp. 315-317.

Fukuchi et al. "Human Placenta-Derived Cells Have Mesenchymal Stem/Progenitor Cell Potential," *Stem Cells*, 2004, vol. 22, pp. 649-658.

Gupta et al. "Intrapulmonary Delivery of Bone Marrow Derived Mesenchymal Stem Cells Improves Survival and Attenuates Endotoxin-Induced Acute Lung Injury in Mice," *J. Immunology*, 2007, vol. 179, pp. 1855-1863.

Ilancheran et al. "Stem Cells Derived from Human Fetal Membranes Display Multilineage Differentiation Potential," *Biology of Reproduction*, 2007, vol. 77, 2007, pp. 577-588.

Int' Anker et al. "Isolation of Mesenchymal Stem Cells of Fetal or Maternal Origin from Human Placenta," *Stem Cells*, 2004, vol. 22, pp. 1338-1345.

Lee et al. "Allogeneic Human Mesenchymal Stem Cells for Treatment of *E. coli* Endotoxin-Induced Acute Lung Injury in the Ex Vivo Perfused Human Lung," *PNAS*, 2009, vol. 106, pp. 16357-16362.

Matikainen et al. "Placenta—An Alternative Source of Stem Cells," *Toxicol. Appl. Pharmacol.*, 2005, vol. 207, pp. 544-549.

Parolini et al. "Isolation and Characterization of Cells from Human Term Placenta: Outcome of the First International Workshop on Placenta Derived Stem Cells," *Stem Cells*, 2007, pp. 1-15.

Ramirez et al. "BIO5192, a Small Molecule Inhibitor of VLA-4, Mobilizes Hematopoietic Stem and Progenitor Cells," *Blood*, 2009, vol. 114, pp. 1340-1343.

Sakuragawa et al. "Human Amnion Mesenchyme Cells Express Phenotypes of Neuroglial Progenitor Cells," *J. Neurosci Res*, 2004, vol. 78, pp. 208-214.

Serikov et al. "Human Term Placenta as a Source of Hematopoietic Cells," *Experimental Biology and Medicine*, 2009, vol. 234, pp. 813-823.

Yen et al. "Isolation of Multipotent Cells from Human Term Placenta," *Stem Cells*, 2005, vol. 23, 2005, pp. 3-9.

\* cited by examiner

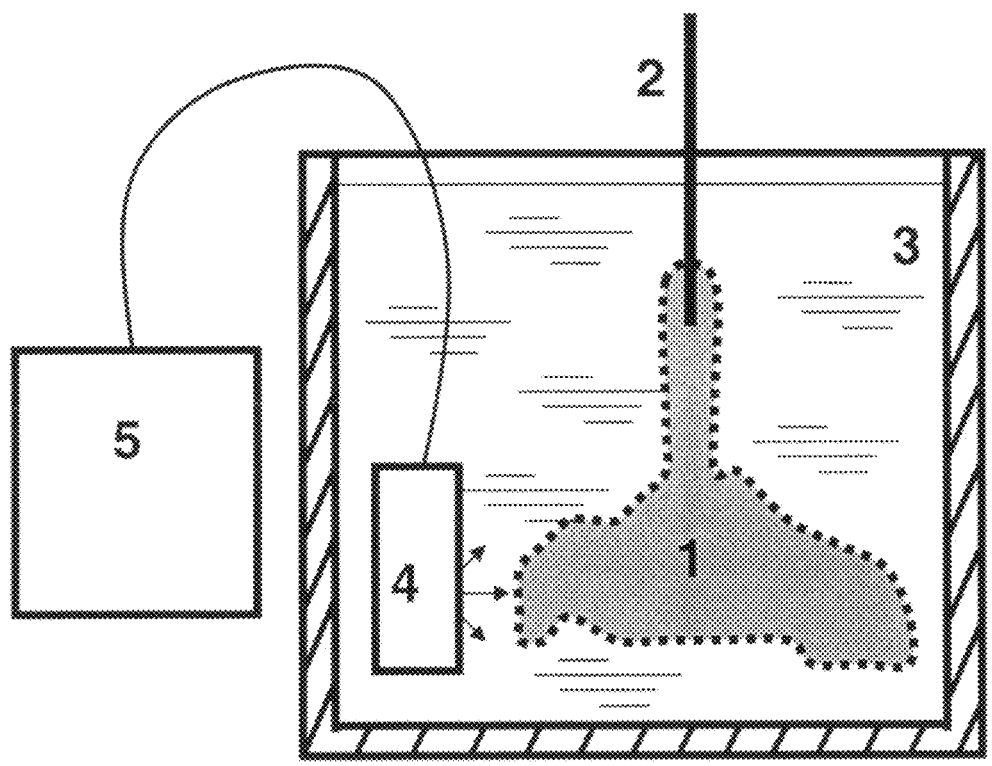

METHODS FOR AUGMENTATION COLLECTION OF PLACENTAL HEMATOPOIETIC STEM CELLS AND USES THEREOF

This application claims the benefit of, and claims priority to, U.S. Provisional Application No. 61/459,922 filed Dec. 22, 2010, which is hereby incorporated herein in its entirety.

FIELD OF THE INVENTION

This invention is directed to methods for augmentation of stem cells collections.

BACKGROUND

Collection and therapeutic use of stem cells is among the most rapidly-developing fields of modern medicine. Ability of stem cells to differentiate into blood lineages is the basis of therapies in many hematological disorders and other medical applications. As of now, only hematopoietic stem cells have been proven to provide therapeutic effect. One of the main problems is the difficulty in obtaining sufficient amounts of stem cells. Therefore, supply of stem cells, including cord blood stem cells is limited, and novel sources are in high demand.

Two major directions in the field of augmentation of stem cells collections could be outlined: novel approaches to stem cell mobilization from known sources, and use of novel sources of stem cells. Most optimal is combination of these two approaches which is the main subject matter of this invention.

Hematopoietic stem cells (HSCs), are multipotent stem cells that give rise to all the blood cell types from the myeloid (monocytes and macrophages, neutrophils, basophils, eosinophils, erythrocytes, megakaryocytes/platelets, dendritic cells), and lymphoid lineages (T-cells, B-cells, NK-cells). The hematopoietic organs contains cells with long-term and short-term regeneration capacities and committed multipotent, oligopotent, and unipotent progenitors. HSCs are a heterogeneous population with different properties, capacities and markers. Many of these markers belong to the cluster of differentiation series, like: CD34, CD38, CD90, CD133, CD105, CD45, and also c-kit;—the receptor for stem cell factor. The HSCs are negative for the markers that are used for detection of lineage commitment.

Mobilization of stem cells is an important step in stem-cell based therapies, especially in treatment of hematological disorders. In adult donors mobilization of hematopoietic stem cells requires puncture of the iliac crest of healthy people who are donating bone marrow. Currently, in clinical practice most often mobilization is performed by administering to the donor growth factors like G-CSF, which activates a cascade of enzymes and complement and releases HSC from its niche. This allows for hematopoietic stem cells to be collected from the peripheral blood.

In general, numerous pharmacological agents mobilize stem cells, ranging from cytokines and growth factors, hormones, to beta-glucans. They differ in their mechanisms of action, some of which are not precisely known, and exert a plethora of effects on both HSCs and their niches. Therefore, pharmacological approach to HSCs mobilization is in general non-specific, and could involve multiple pharmacological agents or their combinations. Stem cells which participate in hematopoiesis are believed to reside in niches in bone marrow in adults. They are hold in place by interaction of multiple adhesion molecules present on the cell surface and surrounding extracellular matrix, or adjacent cells. For example, integrins are molecules that intervene attachments between a cell and the tissues/cells. They also play a role in cell signaling and regulate cellular motility.

There are many types of integrins, and HSCs have multiple types of integrins on their surface. In addition to integrins, other surface proteins such as cadherins, immunoglobulin superfamily cell adhesion molecules, selectins and syndecans mediate cell-cell and cell-matrix interaction and communication. Integrins are heterodimer transmembrane receptors for the extracellular matrix. Natural integrin ligands include laminin, fibronectin, and vitronectin, but they also include fibrinogen and fibrin, thrombospondin, MMP-2, and fibroblast growth factor. Integrin subunits cross the plasma membrane and have short cytoplasmic domains. The molecular mass of the integrin subunits can vary from 90 kDa to 160 kDa. The attachment of the cell is due to formation of multiple cell adhesion complexes, which consist of integrins and many cytoplasmic proteins such as talin, vinculin, paxillin, and alpha-actinin. These proteins regulate kinases such as FAK (focal adhesion kinase) and Src kinase. Adhesion complexes attach to the actin cytoskeleton. Integrins bind ligands by recognizing amino acid stretches on exposed loops, particularly the RGD sequence. Following ligation, integrins mediate signaling events, alone or in combination with growth factor receptors, regulating cell adhesion, and migration by activating canonical pathways, such as integrin-linked kinase (ILK), protein kinase B (PKB/Akt), mitogen-activated protein kinase (MAPK), Rac or nuclear factor kappa B (NF-B). Several classes of integrin inhibitors are currently investigated or used: monoclonal antibodies targeting the extracellular domain of the heterodimer (Vitaxin; MedImmune, Gaithersburg, Md.), synthetic peptides containing an RGD sequence (cilengitide; Merck KGaA, Darmstadt, Germany), and peptidomimetics (S247; Pfizer, St Louis, Mo.), which are orally bioavailable nonpeptidic molecules mimicking the RGD sequence. Natalizumab (Tysabri; Biogen/Idec, Cambridge, Mass., USA) is a recombinant humanized neutralizing IgG4 monoclonal antibody that binds to the ($\alpha_4$-subunit of the $\alpha_4\beta_1$ (VLA-4) and $\alpha_4\beta_7$ integrins. Natalizumab is approved by the FDA for the treatment of Crohn's disease and relapsing Multiple Sclerosis and is postulated to function in these conditions by inhibiting the transmigration of leukocytes through the blood-brain barrier. Following anti-$\alpha_4$ integrin antibody administration, natalizumab-treated MS patients display a rapid and sustained increase in circulating HSPCs (M P Rettig, G Ansstas and J F DiPersio Leukemia advance online publication2 September 2011; doi: 10.1038/leu.2011.197 Mobilization of hematopoietic stem and progenitor cells using inhibitors of CXCR4 and VLA-4). Small-molecule antagonists of $\alpha_4$ integrins is an another way to mobilizing HSPCs. BIO5192 is (2(S)-{[1-3,5-dichloro-benzenesulfonyl)-pyrrolidine-2(S)-carbonyl]-amino}-4-[4-methyl-2(S)-(methyl-{2-[4-(3-o-tolykureido)-phenyl]acetyl}-amino)-pentanoylamino]-butyric acid), a potent ($K_d$ of <10 pM) and highly selective small-molecule inhibitor of both the unactivated and activated forms of $\alpha_4\beta_1$ integrin (P Ramirez, M P Rettig, G L Uy, E Deych, M S Holt, J K Ritchey and J DiPersio. BIO5192, a small molecule inhibitor of VLA-4, mobilizes hematopoietic stem and progenitor cells. Blood, Prepublished online Jul. 1, 2009 doi:10.1182/blood-2008-10-184721).

Stahle and Goodman (WO 2001/010841 Fluorene derivatives as integrin inhibitors) describe fluorine derivatives which can be used as integrin inhibitors for the prophylaxis and treatment of blood disorders and disorders propagated through angiogenesis. U.S. Pat. No. 5,912,266 (Beta integrin cell adhesion molecule inhibitors) describes chemical compound as integrin inhibitor. U.S. Pat. No. 6,849,639 (Integrin inhibitors and their method of use) describes multiple classes of chemical compounds which can be used as integrin inhibitors.

Another example of pharmacological agent used for cell mobilization is a blocker of CXCR4 receptor under the trademark name AMD3100 (USPTO trademark serial number 78367683). AMD3100, or Plerixafor is pharmaceutical and medicinal preparations for the treatment of HIV, inflammation, arthritis, asthma, cancer, cell transplants and cell transplant rejection, organ transplants and organ transplant rejection, angiogenesis, multiple sclerosis, bacterial infection, peripheral blood stem cell mobilization, cardiovascular disease, leukemia, drug-induced anemia, retrovirus, hematopoietic deficit resulting from chemotherapy or radiation therapy, and elevation of white blood. AMD3100 is a partial antagonist of the alpha chemokine receptor CXCR4. The CXCR4 alpha-chemokine receptor and one of its ligands, SDF-1, are important in hematopoietic stem cell homing. Plerixafor has been found to be a strong inducer of mobilization of hematopoietic stem cells from the bone marrow to the bloodstream as peripheral blood stem cells Cashen, A. F.; Nervi, B.; Dipersio, J. (2007). "AMD3100: CXCR4 antagonist and rapid stem cell-mobilizing agent". *Future Oncology* 3 (1): 19-27.

Apart from pharmacological factors, physical factors are also capable to affect homing and release of stem cells from their niches. Most convenient practical examples of such physical factors are ultrasound and electromagnetic fields. Ultrasound is cyclic sound pressure with a frequency greater than the upper limit of human hearing (approximately 20 kHz). The ultrasound is used to penetrate a medium and measure the reflection signature or supply focused energy. The reflection signature can reveal the inner structure of the medium, and is usually used in medicine for diagnostical purposes (sonography). Ultrasound also has therapeutic applications (to treat stone diseases of internal organs—lithotripsy). High Intensity Focused Ultrasound is used ultrasound to ablate tumors or other tissue non-invasively in which lower frequencies than medical diagnostic ultrasound is used (25-200 kHz), but higher time-averaged intensities. Delivering chemotherapy to cancer cells and other tissues is called acoustic targeted drug delivery which uses high frequency ultrasound (1-10 MHz) and a range of intensities 0-20 W/cm$^2$. The acoustic energy is focused on the tissue of interest to agitate its matrix and make it more permeable. Additional physiological effects of low-intensity ultrasound have been used to stimulate bone-growth and its potential to disrupt the blood-brain barrier for drug delivery. Low intensity pulsed ultrasound is used for therapeutic tooth and bone regeneration. Ultrasound in the low MHz range in the form of standing waves is a new approach to achieve a tool for separation of cells in tissues and culture, concentration and directional movement of small particles and cells. This method has specific name "acoustophoresis". The basis of "acoustophoresis" is the acoustic radiation force, a non-linear effect which causes particles to be attracted to either the nodes or anti-nodes of the standing wave depending on the acoustic contrast factor, which is a function of the sound velocities and densities of the particle and of the medium in which the particle is immersed. U.S. Pat. application Ser. No. 20070065420 (Ultrasound therapy resulting in bone marrow rejuvenation) describes a method and system for treating a patient to repair damaged tissue which includes exposing a selected area of bone marrow of a patient to ultrasound waves or ultra shock waves so that cells comprising stem cells, progenitor cells or macrophages are generated in the area of the bone marrow of the patient due to the ultrasound, converting the cells from the bone marrow of the patient and reducing the damaged tissue in the bone marrow of the patient by repairing the damaged tissue.

An electromagnetic field is a physical field produced by the motion of electrically charged objects. It affects the activities of charged particles and objects in the vicinity of the field. Magnetic fields arise from the motion of electric charges. Low-frequency electric fields influence the human body same as they influence any other material made up of charged particles. They cause current to flow through the body to the ground. Low-frequency magnetic fields induce circulating currents within the human body. The strength of these currents depends on the intensity of the outside magnetic field. If sufficiently large, these currents could cause stimulation of cells or affect other biological processes. Heating is the main biological effect of the electromagnetic fields of radiofrequency fields. Therefore, ultrasound and electromagnetic fields represent additional approach for HSCs mobilization.

HSCs and hematopoietic progenitor cells (HPCs) are widely used for transplantation treatment of blood cell disorders. Bone marrow, peripheral blood, and umbilical cord blood (CB) currently serve as sources of HSCs for transplantation, but the demand for HLA-matched stem and progenitor cells exceeds the supply; less than 50% of patients today are able to obtain needed allogeneic transplantations. As less than 30 percent of potential recipients have HLA-identical siblings, transplantation of allogeneic HSCs is widely used. Allogeneic transplantation of bone marrow or HSCs-enriched peripheral blood often results in a severe adverse immunologic response. Umbilical cord blood is a potential source of HSCs and HPCs, but limited numbers of HSCs per CB unit limit the use of CB for transplantation to small children. Alternative sources of HSCs are, therefore, in high demand for treatment of adults.

Cells isolated from umbilical cord—anatomical structure which connects a baby with placenta—have been described in several patents. Messina et al., (U.S. Pat. No. 7,524,489 "Regeneration and repair of neuronal tissue using postpartum-derived cells"), teaches method of treatment patients with cells derived from umbilical cord which do not express CD117 while expressing oxidized LDL receptor1, interleukin 8 or reticulon 1. Mistry et al., (U.S. Pat. No. 7,510,873 "Postpartum cells isolated from umbilical cord tissue, and methods of making and using the same") teaches method of isolation of a cell from umbilical cord by enzymatic digestion that does not express CD117, CD31, CD34, CD141 or CD45 and express CD10, CD13, CD44, CD73, CD90, PDGFr-alpha or HLA-A, and further teaches use of these cells for treatment of retinitis (Mistry et al., U.S. Pat. No. 7,413,734 "Treatment of retinitis pigmentosa with human umbilical cord cells"). Harmon et al. (U.S. Pat. No. 7,560,276 "Soft tissue repair and regeneration, using postpartum-derived cells") teaches use of these cells from umbilical cord and their products for soft tissue repair. Davies et al., U.S. Pat. No. 7,547,546 "Progenitor cells from Wharton's jelly of human umbilical cord" teaches obtaining cells from umbilical cord and their use in tissue repair. Use of proteolytic enzymes required for all the above described methods, first, dramatically reduces cell viability and yield of colony-forming unit cells, and, second, eliminates expression of many stem cell markers on cell surface, thus not allowing using sorting techniques for isolation of stem cells. The above described methods to obtain cells from umbilical cord feature same problems as obtaining stem cells from other low volume sources—yield of viable colony-forming unit cells from this source is very low.

Hariri (U.S. Pat. No. 7,045,148) reports that the first collection of blood from the perfused placenta, referred to as cord blood, contains populations of hematopoeitic progenitor cells which are CD34 positive and CD38 positive or CD34 positive and CD38 negative or CD34 negative and CD38 positive. Subsequent perfusions of the placenta were reported to yield embryonic-like stem cells that are SSEA-3 negative, SSEA-4 negative, Oct-4 positive, ABC-p positive, CD10 positive, CD38 negative, CD29 positive, CD34 negative, CD44 positive, CD45 negative, CD54 positive, CD90 positive, SH2 positive, SH3 positive and SH4 positive. Hariri (U.S. Pat. No. 7,311,905 "Embryonic-like stem cells derived from post-partum mammalian placenta, and uses and methods of treatment using said cells") describes a composition of human stem or progenitor cells that are positive for SH2, SH3, SH4 and Oct-4, while negative for CD34, CD45, SSEA3 and SSEA4, and obtained from placenta that has been drained from cord blood. Cells could express at least one of the following markers: CD10, CD29, CD44, CD54, CD90. Hariri (U.S. Pat. No. 7,468,276 "Placental stem cells") describes the same placental stem cell population, adherent to plastic. Hariri (U.S. Pat. No. 7,255,879 "Post partum mammalian placenta, its use and placental stem cell populations") teaches method to obtain the above described placental stem cell population by perfusing placenta via circulation with a perfusion solution containing an anticoagulant, growth factor or cytokine selected from a group consisting of a colony stimulating factor, interferon, erythropoietin, stem cell factor, thrombopoietin, an interleukin, granulocyte colony-stimulating factor, and any combination thereof, and collection of cells from perfusate. Methods of directed differentiation of these cells are described by Hariri (U.S. Pat. No. 7,498,171 "Modulation of stem and progenitor cell differentiation, assays and uses thereof").

The main disadvantage of methods described by Hariri in the above cited patents is in the fact that long-term perfusion of placenta is required to obtained claimed cells. It is know to those skilled in arts that in most cases of placentas obtained by Caesarian section and in all cases of placentas collected following natural birth, placentas are ruptured. This precludes the possibility of the long-term perfusion, as perfusate is rapidly lost via ruptures of chorion; therefore, long-term perfusion becomes impracticable. In most cases, arteries of umbilical cord rapidly completely constrict, and as thrombosis develops in placental vessels perfusion of placenta by techniques claimed by Haririr's patents (U.S. Pat. Nos. 7,045,148; 7,255,879; 7,311,905; 7,468,276) becomes practically impossible. Most importantly, perfusion of placenta via natural circulation does not allow collecting populations of stem cells which are located in stroma, interstitial tissue or non-perfused regions of placental circulation. Therefore, placental perfusion and cells claimed by Hariri's patents (U.S. Pat. Nos. 7,045,148; 7,311,905; 7,468,276; 7,498,171) allow obtaining very restricted and limited cell populations present in placenta, which belong to pool located inside the circulatory space. It is, therefore, a subject matter of this invention to disclose novel techniques, methods and stem cell populations which could be obtained without placental perfusion.

Recently several patents described an improved way to obtain additional amounts of cord blood and different types of stem cells by perfusion of placenta. Hariri (U.S. Pat. No. 7,045,148) reports that the first collection of blood from the perfused placenta, referred to as cord blood, contains populations of hematopoeitic progenitor cells. U.S. patent application Ser. No. 20100248206 (Method of Isolating Stem and Progenitor Cells From Placenta) describes a method for cryopreserving fetal stem and progenitor cells in a mammalian placenta, the method comprising: perfusing a mammalian placenta with a perfusion solution comprising an anti-coagulant, a vasodilator, and a cryopreservative agent. Serikov et al (Human term placenta as a source of hematopoietic cells, Exp Biol Med 2009, 234:813-823) reported that the human placenta contains large numbers of CD34-expressing hematopoietic cells, with the potential to provide a cellular yield several-fold greater than that of a typical cord blood harvest. Cells from placental tissue generated erythroid and myeloid colonies in culture, and also produced lymphoid cells after transplantation in immunodeficient mice. AMD3100 was used to mobilize cells from placenta during 6-8 hour vascular perfusion, which allowed to inclearse yeaild of HSC from perfusate several-fold as compared to cord blood unit HCSs.

Procedures described by Hariri and others and termed as "perfusion" require putting catheters into umbilical vein and artery, and securing these catheters in place to avoid loss of perfusate. Such procedure which specifically includes placement of catheters into umbilical arteries requires very highly skilled professional to perform and in large number of cases is simply impossible. Perfusion requires complex and expensive set of equipment, continuous control of trained personnel and is impossible to perform in field conditions. Moreover, as most of cord blood units are collected in hospitals, the processing and storage happens at a few specialized centers. Therefore, shipment of material by mail is required. Such step in cord blood collection process makes perfusion of placenta to obtain HSCs practically impossible for large scale operations. Therefore, there is a need for a method, which will allow collection of HSCs from placental circulation without the need for perfusion of placenta. The present invention addresses this need and provides further related advantages.

It also the object of the present invention to provide a method of mobilizing HSCs from placenta utilizing physical means of ultrasound wave field application, and or pulsed electromagnetic field application.

SUMMARY OF THE INVENTION

The subject matter of this invention is a novel method to obtain populations of placental hematopoietic stem and progenitor cells in abundant numbers for use in medical practices.

In one specific embodiment HSCs and HPCSs of human placenta are obtained from placenta by delivery of cell-liberating compounds, incubation of placenta under specific conditions and obtaining cells by effusion.

In another specific embodiment HSCs and HPCSs of human placenta are obtained from placenta by delivery of cell-liberating compounds, incubation of placenta under specific conditions, application of electro-magnetic fields to placenta and obtaining cells by effusion.

In yet another specific embodiment HSCs and HPCSs of human placenta are obtained from placenta by delivery of cell-liberating compounds, incubation of placenta under specific conditions, application of ultrasound fields to placenta and obtaining cells by effusion.

In yet another specific embodiment hematopoietic HSCs and HPCSs of human placenta are obtained from placenta by application of electromagnetic or ultrasound fields to placenta and obtaining cells by effusion.

In yet another preferred embodiment, HSCs and HPCSs of human placenta are obtained from placenta by delivery of cell-preservation compounds to placenta and cell-liberating compounds, incubation of placenta under specific conditions and obtaining cells by effusion.

In yet another specific embodiment HSCs and HPCSs of human placenta are multipotent stem cells that give rise to all the blood cell types from the myeloid (monocytes and macrophages, neutrophils, basophils, eosinophils, erythrocytes, megakaryocytes/platelets, dendritic cells), and lymphoid lineages (T-cells, B-cells, NK-cells) and are a heterogeneous population with different properties, capacities and markers which in general may display one or several of the following surface markers: $CD34^+$, $CD45^{dim}$, $CD133^+$, $CD59^+$, $Thy1/CD90^+$, $CD38I^{low}$, $CD117^+$.

In yet another embodiment, a cell-based therapeutic composition of an effective amount of cells obtained from placenta is transplanted into a body for enhancing regeneration in hematological disorders by repopulating bone marrow, regeneration of diseased tissue of different organs, alterations in blood supply (ischemia, thrombosis, atherosclerosis), by local or systemic delivery of cells which is based upon expression of growth factors and cytokines stimulating tissue regeneration, independent of engraftment.

In yet another embodiment, a cell-based therapeutic composition comprising an effective amount of hematopoietic stem or progenitor cell is used for enhancement of regeneration of vascular system by local or systemic delivery of vascular endothelial cells, which is based upon homing to damaged organ and release of growth factors and cytokines independent of engraftment, or based upon engraftment and differentiation of said cells into one of the specific cell lineages of organs or tissues of cardiovascular system.

In yet another embodiment, a cell-based therapeutic composition comprising an effective amount of hematopoietic stem or progenitor cell is used for treatment of senescence processes in organ or in a body which is based upon homing to damaged organ and release of growth factors and cytokines independent of engraftment, or based upon engraftment and differentiation of said cells into one of the specific cell lineages of organs or tissues of aging body.

DEFINITIONS

As used herein, the term "stem cell" or "colony-forming unit cell" refers to an undifferentiated cell that can be induced to proliferate. The stem cell is capable of self-maintenance or self-renewal, meaning that with each cell division, one daughter cell will also be a stem cell. Stem cells can be obtained from embryonic, post-natal, juvenile, or adult tissue. Stem cells can be pluripotent or multipotent. The term "progenitor cell," as used herein, refers to an undifferentiated cell derived from a stem cell, and is not itself a stem cell. Some progenitor cells can produce progeny that are capable of differentiating into more than one cell type. Hematopoietic stem cells (HSCs), are multipotent stem cells that give rise to all the blood cell types from the myeloid (monocytes and macrophages, neutrophils, basophils, eosinophils, erythrocytes, megakaryocytes/platelets, dendritic cells), and lymphoid lineages (T-cells, B-cells, NK-cells). HSCs are a heterogeneous population with different properties, capacities and markers. Human HSC are in general characterized by the presence of the following surface markers: $CD34^+$, $CD133^+$, $CD59^+$, $Thy1/CD90^+$, $CD38I^{low}$, $CD117+$, $lin^-$.

Term "infusion" refers to a method of delivery of fluids, compositions, drugs, solutions to tissue and its cellular and extracellular components and vascular bed without simultaneous effusion. Term "perfusion" refers the process of continuous delivery of blood or its substitute—"perfusate" to the capillary bed of tissue with simultaneous continuous effusion. Term "effusate" refers to fluids obtained from placenta following infusion or perfusion.

Term "cell-liberating compounds" refers to chemicals, peptides, antibodies which specifically or non-specifically block adhesion molecules or receptors which control adherence of cells to its niche in vascular bed or in connective tissue. Include specific or non-specific receptor blockers of CXCR4 receptors (AMD3100, T-140 and alike), multiple integrin inhibitors, antibodies and peptides against beta-2 integrins, biologically-compatible detergents, antibodies or blocking peptides to ICAM-1, VCAM.

Term "cell-preservation compounds" includes a vast group of components which preserve integrity of cell membranes and prevent cells from oxidative injury and apoptosis. These groups include multi-component solutions know to those skilled in arts as "University of Wisconsin solution", "Celsior solution" and alike, calmodulin inhibitors (Chlorpromazine and alike); calcium channel blockers (nifedipine, verapamil, papaverine and alike); vasoactive drugs (Prostacycline, prostaglandins, magnesion ions), protease and phospholipase inhibitors (Chlorpromazine and alike, verapamil and alike, aprotinin, pepstatin and alike); antioxidants (glutathione, SOD, N-acetyl-cysteine, Methylene Blue dye, allopurinol, Vitamins E and C and alike); anti-apoptotic compounds (LXR-015, cycloheximide and alike); membrane stabilizers (Chlorpromazine, dexamethazone and alike); hormones; cytoprotectors (glycine and alike), sugars, nucleotide precursors (adenine, adenosine and alike), oxygen carriers (perfluorocarbons and alike), growth factors and cytokines.

As used herein, the terms "treatment," "treating," and the like, refer to obtaining a desired pharmacologic and/or physiologic effect. The effect may be prophylactic in terms of completely or partially preventing a disease or symptom thereof and/or may be therapeutic in terms of a partial or complete cure for a disease and/or adverse affect attributable to the disease. "Treatment," as used herein, covers any treatment of a disease in a mammal, particularly in a human, and includes: (a) preventing the disease from occurring in a subject which may be predisposed to the disease but has not yet been diagnosed as having it; (b) inhibiting the disease, i.e., arresting its development; and (c) relieving the disease, i.e., causing regression of the disease. The terms "individual," "subject," "host," and "patient," used interchangeably herein, refer to a mammal, including, but not limited to, murines (rats, mice), non-human primates, humans, canines, felines, ungulates (e.g., equines, bovines, ovines, porcines, caprines), etc. A "therapeutically effective amount" or "efficacious amount" means the amount of a compound or a number of cells that, when administered to a mammal or other subject for treating a disease, is sufficient to effect such treatment for the disease. The "therapeutically effective amount" will vary depending on the compound or the cell, the disease and its severity and the age, weight, etc., of the subject to be treated.

The term "antibody" includes antibody of any of various isotypes; polyclonal antibodies; monoclonal antibodies; antigen-binding fragments of a monoclonal antibody (e.g., Fab, Fv, scFv, and Fd fragments); chimeric antibodies; humanized antibodies; single-chain antibodies; etc.

This invention is not limited to particular embodiments described, such may vary.

BRIEF DESCRIPTION OF THE DRAWINGS

FIG. 1. Method of obtaining HSCs from placenta. Placenta (1) is filled with a composition comprising one or more agents selected from the group consisting of a cell preservation compound and cell adhesion receptor blocker to provide infused placental tissue via vessel (2) and placed in reservoir (3). Placenta is incubated in reservoir (3) and exposed to ultrasonic radiation from ultrasound source (4) connected to energy source (5), following which hematopoietic stems cells are eluted from the incubated placental tissue.

DETAILED DESCRIPTION OF THE INVENTION

The present invention describes novel methods for obtaining HSCs or HPSs from a mammalian placenta by filling placental circulation with cell liberating compounds, which include specific or non-specific receptor blockers of CXCR4 receptors (AMD3100, POL-6329, BTK-140, TG-0054, MDX-1338, and alike), integrin inhibitors and alike, antibodies and blocking peptides against beta-2 integrins, SDF-1, VCAM, ICAM-1 (CD54), biocompatible detergents (Tyloxapol (WR-1339) and alike. Cells could be derived from the vasculature following incubation of tissue with compositions containing cell-liberating compounds.

The methods generally involve: a) obtaining placenta; b) infusion of the cell-liberating composition into placental tissue, c) subjecting the placenta to ultrasound or electromagnetic field, and d) obtaining effusate. A placenta is obtained following natural birth or Caesarean section, e.g., from one minute to about one hour following birth. For example, a mammalian placenta is obtained from about one minute to about 5 minutes, from about 5 minutes to about 10 minutes, from about 10 minutes to about 20 minutes, from about 20 minutes to about 30 minutes, from about 30 minutes to about 45 minutes, or from about 45 minutes to about 60 minutes following birth.

The infusion solution for placenta includes an anti-coagulant, a vasodilator, and a cell-liberating composition. The infusion or perfusion solution can also include one or more of dissolved oxygen, carbon dioxide, and an inert gas. Suitable anti-coagulants include, but are not limited to, heparin, e.g., unfractionated heparin, low molecular weight heparin (e.g., Lovonox, Fragmin, Anti-XA, Axrista, etc.); ethylenediamine tetraacetic acid (EDTA); hirudin, a hirudin analog, refludin (Refludan, recombinant hirudin), bivalirudin (Angiox); a coumarin, e.g., warfarin (4-hydroxycoumarin); a thrombin inhibitor; a coagulation factor inhibitor; a protein C pathway component; a tissue factor pathway inhibitor; an anti-platelet compound; a platelet aggregation inhibitor; a fibrinolytic pathway component; acetylsalicylic acid; and the like For example, suitable anti-coagulants include, e.g., acenocoumarol, ancrod, anisindione, bromindione, clorindione, coumetarol, cyclocumarol, dextran sulfate sodium, dicumarol, diphenadione, ethyl biscoumacetate, ethylidene dicoumarol, fluidione, heparin, hirudin, lyapolate sodium, oxazidione, penstosam polysulfate, phenindione, phenprocoumon, phosvitin, picotamide, tioclomarol, and warfarin. Suitable anti-coagulants include those that, at the concentrations/amounts used, do not have significant adverse effects on the viability of a stem/progenitor cell present in the placenta.

A suitable amount of an anti-coagulant can be in a range of from about 1 U/ml to about 100 U/ml, e.g., from about 1 U/ml to about 5 U/ml, from about 5 U/ml to about 10 U/ml, from about 10 U/ml to about 20 U/ml, from about 20 U/ml to about 30 U/ml, from about 30 U/ml to about 50 U/ml, from about 50 U/ml to about 75 U/ml, or from about 75 U/ml to about 100 U/ml.

Suitable vasodilators include, but are not limited to, papaverin, moxaverin, hydralazine (e.g., hydralazine hydrochloride; 1-hydrazinophthalazine monohydrochloride; Apresoline®), dihydralazine, minoxidil (3-hydroxy-2-imino-6-(1-piperidyl)pyrimidin-4-amine), nitroglycerin, isosorbide dinitrate, diazoxide, nitroprusside, diltiazem, amiodarone, isoxsuprine, nylidrin, tolazoline (2-benzyl-4,5-dihydro-1H-imidazole), and verapamil. Suitable vasodilators include those that, at the concentrations/amounts used, do not have significant adverse effects on the viability of a stem/progenitor cell present in the placenta.

Suitable cell-liberating compound solution comprises an agent that induces mobilization of a stem and/or progenitor cell, its detachment from vascular or tissue niche. Agents that induce mobilization of a stem and/or progenitor cell include, but are not limited to, a biocompatible, non-ionic surfactant.

In preferred embodiments, the HSCs/HPCs mobilization agent is a CXCR4 antagonist such as AMD-3100 or a derivative or analog thereof. AMD-3100 (1,1'-[1,4-phenylene-bis (methylene)]-bis-1,4,8,11-tetraazacyclotetradecane) is described in U.S. Pat. No. 5,583,131. Also suitable for use are derivatives and analogs of AMD-3100, can be present in the stem/progenitor cell collection solution at a concentration of from about 1 mg/L to about 100 mg/L.

In another preferred embodiment the HSCs/HPCs mobilization agent is from the group of integrin inhibitor.

In another preffered embodiment the HSCs/HPCs mobilization agent is from the group of proteolytic enzymes, including but not limited to trypsin, collagenase, streptokinase, urokinase, lidase, dispase, liberase and alike.

In another preferred embodiments the HSCs/HPCs mobilization agent is a chelating compound, including but not limited to EDTA, EGTA and alike.

In preferred embodiments, antibodies that can be included in a stem/progenitor cell collection solution include an antibody that is specific for a cell adhesion molecule and that, when bound to the cell adhesion molecule, inhibits cell adhesion mediated by the cell adhesion molecule. Adhesion molecules include, e.g., an intracellular adhesion molecule (ICAM) (e.g., ICAM-1); a vascular cell adhesion molecule (VCAM; CD106), a plateletendothelial cell adhesion molecule (PECAM); an integrin; a cadherin; and a selectin. Any antibody that specifically binds to an adhesion molecule, and that, when bound to the adhesion molecule, inhibits cell adhesion mediated by the cell adhesion, is suitable for use. Several such antibodies are known and can be used.

Biocompatible surfactants, e.g., benzalkonium chloride, cetylpyridinium chloride, an alkylaryl polyether alcohol (e.g., tyloxapol), various polysorbates (e.g., polysorbate 80, polysorbate 20), and further polyethoxylated substances and poloxamers (e.g., poloxamer 282). Biocompatible surfactants include nonionic, cationic, ionic, and zwitterionic surfactants. Suitable non-ionic surfactants include, but are not limited to, diacetylated monoglycerides, diethylene glycol monostearate, ethylene glycol monostearate, glyceryl monooleate, glyceryl monostearate, propylene glycol-monostearate, macrogol esters, macrogol stearate 400, macrogol stearate 2000, polyoxyethylene 50 stearate, macrogol ethers, cetomacrogol 1000, lauromacrogols, nonoxinols, octoxinols, tyloxapol, poloxamers, polyvinyl alcohols, polysorbate 20, polysorbate 40, polysorbate 60, polysorbate 65, polysorbate 80, polysorbate 85, sorbitan monolaurate, sorbitan monooleate, sorbitan monopalmitate, sorbitan monostearate, sorbitan sesquioleate, sorbitan trioleate, sorbitan tristearate and sucrose esters. In preferred embodiments, the non-ionic surfactant is Tyloxapol. Tyloxapol is a 4-(1,1,3,3-tetramethylbutyl)-phenol polymer with ethylene oxide and formaldehyde (also known as tyloxapol). Tyloxapol is also known as Triton WR-1339 and was described by Serikov (U.S. Pat. No. 5,658,560) as a non-specific biocompatible cell receptor blocker. In these embodiments, Tyloxapol is present in the stem/progenitor cell collection solution at a concentration of from about 20 mg/L to about 2500 mg/L.

The infusion solution can also include antioxidants for prevention of post-re-warming cell oxidative stress. Suitable anti-oxidants include but are not limited to: N-acetyl-cysteine, cysteine, methyonine, Methylene Blue dye, glutathione, vitamin C, and vitamin E, as well as enzymes such as catalase, superoxide dismutase and various peroxidases and peroxiredoxins.

In some embodiments, the infusion solution can further comprise one or more of an anti-microbial agent, a growth factor, and a cytokine. Suitable anti-microbial agents include, but are not limited to, agents that inhibit growth and/or viability of Gram positive bacteria; agents that inhibit growth and/or viability of Gram negative bacteria; agents that inhibit growth and/or viability of acid-fast bacilli (e.g., mycobacteria); agents that inhibit growth and/or viability of a yeast or fungal cell; agents that inhibit growth and/or viability of a protozoa; and the like. Suitable anti-microbial agents include, but are not limited to, β-lactam antibiotics, e.g., penicillin, derivatives and analogs of penicillin, cephalosporin, etc.; carbapenems; aminoglycosides, e.g., streptomycin, kanamycin, and the like; macrolide antibiotics, e.g., erythromycin, tylosin, etc.; bacitracin; gramicidin; mupirocin; chloramphenicol; thiamphenicol; fusidate sodium; lincomycin; clindamycin; novobiocin; polymyxins; rifamycins; spectinomycin; tetracyclines; vancomycin; teicoplanin; streptogramins; anti-folate agents including sulfonamides, trimethoprim and its combinations and pyrimethamine; synthetic antibacterials including nitrofurans, methenamine mandelate and methenamine hippurate, nitroimidazoles, quinolines, fluoroquinolones, isoniazid, ethambutol, pyrazinamide, para-aminosalicylic acid (PAS), cycloserine, capreomycin, ethionamide, prothionamide, thiacetazone and viomycin. Suitable anti-microbial agents include those that, at the concentrations/amounts used, do not have significant adverse effects on the viability of a stem/progenitor cell present in the placenta.

The mammalian placenta is infused with the stem/progenitor cell-liberating solution for a period of time from about 5 minutes to about 12 hours, e.g., from about 5 minutes to about 1 hour, from about 1 hour to about 2 hours, from about 2 hours to about 3 hours, from about 3 hours to about 4 hours, from about 4 hours to about 6 hours, from about 6 hours to about 8 hours, or from about 8 hours to about 12 hours.

Following incubation, the HSCs and HPCs of the current invention could be collected and characterized, as illustrated by Example 1.

Solution for infusion could be saturated with oxygen, carbon dioxide or inert gases.

Solution for infusion could be at near zero (C) degree temperature, room temperature, body temperature (37° C.) or in between.

As infusion solution, a variety of isotonic solutions (phosphate-buffered saline-PBS, and alike) or media for cell growth known to those skilled in arts could be used. For example, MEM, DMEM, F12, RPMI-1640, alpha-MEM with or without 0.5-2.5 mM L-glutamine, and with or without fetal bovine serum (FBS), with or without antibiotics like penicillin/streptomycin or others alike. A variety of additional growth factors and supplements, could be used as supplements.

The infusion solution includes one or all from groups of an anti-coagulant, a vasodilator, and a cell-liberating composition.

In another preferred embodiments the mammalian placenta is subjected to ultrasound with frequency ranging 20 kHz to 20 MHz, e.g., from about 20 kHz to about 200 kHz, from about 200 KHz to about 1 MHz, from about 1 MHz to about 5 MHz, from about 5 MHz to about 20 MHz. A range of intensities 0.1-20 W/cm$^2$ for ultrasound could be used.

In another preferred embodiments the mammalian placenta is subjected to varying electromagnetic field from approximately 0.05 gauss to approximately 1 gauss for a varying period of time.

In preferred embodiments placenta is placed in liquid filled container for ultrasound or electromagnetic treatment (as illustrated in FIG. 1) for a period of time from about 5 minutes to about 12 hours, e.g., from about 5 minutes to about 1 hour, from about 1 hour to about 2 hours, from about 2 hours to about 3 hours, from about 3 hours to about 4 hours, from about 4 hours to about 6 hours, from about 6 hours to about 8 hours, or from about 8 hours to about 12 hours.

In preferred embodiments following a period of placenta incubation for a sufficient period of time after infusion of solution in placental vessels and/or application of ultrasound or electromagnetic field, cells are collected from circulation by collection of fluids from placental circulation. Fluids could be collected by methods known to those skilled in art by fields of gravity (placement of placenta above the collection vessel or centrifuging the placenta), by external physical pressure, by flushing fluids out of placental circulation by means of infusion fluids into artery or vein and collecting fluids with cells coming out of the opposite vessel. Cells obtained by these procedures could be further characterized as demonstrated in Examples 2 and 3.

After collection of the cell suspension from the placenta, the cells could be separated from the fluid part by centrifugation, filtration, absorption, apheresis, absorption with assistance of magnetic beads or other means known to those skilled in arts. Following separation, cells could be processes for further storage, freezing or immediate use in patients.

As is shown by Examples 1-3, collected HSCs from placenta by the method of this invention show the phenotype (CD34$^+$CD45$^{dim}$) and properties to form colonies of erythrocytes, leukocytes and megacaryocytes in culture, as well as repopulate immunodeficient mice as human blood lineages which are indistinguishable from HSCs of cord blood. This evidence indicates that placental HSCs obtained by the method of the current invention could be used in humans in the same fashion as cord blood cells for the treatment of blood disorders in various conditions.

Utility: therapeutic use of HSCs and HPCs of the current invention. Pharmaceutical compositions comprising stem cells of the current invention or their derivatives could be administered to a human using multiple cells culture carriers well known to those skilled in arts. Composition depends upon the target organ and route of administration. Cells could be delivered systemically, via artery or vein, or locally, using instillation into a wound, airways, application to the skin or infusion or injections into tissues by means of catheter or needle. Carriers could be chosen from a variety of media solutions used for cell culture.

Clinical applications of the collected placental cells include treatment of a disorder in an individual (e.g., a human). For example, collected HSCs and HPCs, or progeny thereof, can be introduced into an individual in need thereof, to treat a condition or disorder. The individual can be a neonate (e.g., an individual in an age range of from about one week to about one month), an infant (e.g., an individual in an age range of from about one month to about 12 months), a toddler (e.g., an individual in an age range of from about 12 months to about 3 years), a child in an age range of from about 3 years to about 8 years, a pre-teenager (e.g., an individual in an age range of from about 9 years to about 12 years), a teenager (e.g., an individual in an age range of from about 13 years to about 19 years), an adult (e.g., an individual 20 years old or older), a geriatric patient (e.g., an individual in an age range of from about 65 years to 100 years or older); etc.

Collected HSCs and HPCs, or progeny thereof, can be used to provide tissues for grafting such as bone marrow, skin, cartilage, tendons, bone, muscle (including cardiac muscle), blood vessels, cornea, neural cells, gastrointestinal cells, etc. HSCs and HPCs from placenta could be introduced into the body either systemically (intravenous or intra-arterial infusion), or locally, using standard way of delivery like injection with the needle or catheter.

Cell lines and primary cells of the current invention may be used specifically for the purpose of treatment of Acute Lung Injury or Adult Respiratory Distress Syndrome, or Bacterial Pneumonia. Acute Lung Injury (ARDS) is characterized by profound alterations in lung circulation with the following alterations of permeability of endothelial and epithelial barriers, accumulation of protein-rich edema fluid in alveolar spaces, development of pulmonary insufficiency and results in subsequent death in 40-60% of cases. Often ARDS is the result of viral or bacterial pneumonia, sepsis, multi-organ insufficiency. Survivors of ARDS in 50% of cases develop debilitating Pulmonary Fibrosis. Introduction of HSCs and HPCs described by this invention at the dose $0.5-5 \times 10^6$ cells/per kg results in increased survival, decrease in a degree of lung edema and excess lung water, absence of histo-pathological lung injury without evidence of engraftment of cells of the current invention, as shown in details in Example 4. Following local or systemic administration, cells of the current invention are found in thymus, bone marrow, spleen and liver. Therapy with cell significantly shifts balance of pro- and anti-inflammatory cytokines and thus significantly reduces mortality in Adult Respiratory Distress Syndrome and Acute Lung Injury.

A bone fracture is a break in the continuity of the bone, which occurs as a result of mechanical stress or certain medical conditions that weaken the bones, such as osteoporosis, cancer, or osteogenesis imperfecta. The natural process of healing a fracture starts when the bleeding from injured bone forms a fracture hematoma. A blood clot situated between the broken bone fragments, and vessels grow into the clot from a bone and surrounding tissue. Blood cells like monocytes and macrophages remove the non-viable material. Fibroblasts of different origin appear in the walls of the vessels and, following proliferation, produce collagen fibers. Fibroblasts lay down bone matrix (calcium hydroxyapatite) in the form of insoluble crystals. The initial "woven" bone does not have the strong mechanical properties, but by remodeling, the woven bone is substituted by mature "lamellar" bone. This process can take up to 12-24 months, depending on the age of person, type of bone and type of fracture. In some cases, where fracture is infected, fragments move, muscle or other material is positioned between fragments, healing of fracture may never happen with formation of a "pseudo-joint." Treatment is aimed to ensure the best possible function of the injured bone after healing. Bone fractures are typically treated by restoring the position of fractured pieces, and maintaining those positions. If being treated by surgical procedures, nails, wire, and screws are used to hold the fractured bone together more directly. Bone tissue is predominantly extracellular matrix, and as blood vessels are needed to support bone metabolism, formation of blood vessels is extremely important in bone healing. Multiple disorders including infections, diabetes, immunological abnormalities, malnutrition, metabolic disorders, circulatory diseases, old age slow down the process of bone healing, sometimes making it impossible to heal bone fractures.

HSCs and HPCs of the current invention may be used for the purpose of treatment of bone fractures due to their ability to facilitate formation of vessels and enhance regeneration of tissue by stimulating cell proliferation as illustrated in details in Example 5. Introduction of HSCs and HPCs of the current invention at the dose $5-50 \times 10^6$ cells at the site of bone fracture results in enhanced rate of regeneration of bone defect with rapid restoration of bone structure, as illustrated in detail in Example 5. This restoration occurs due to a massive release by the cells of current invention of multiple growth factors, including but not limited to HGF, FGF, KGF, VEGF, GM-CSF, SCF, and angiopoietins.

Tissue ischemia is a condition characterized by restriction of blood supply. Causes of ischemia are mostly related to diseases of blood vessels, resulting in damage to the tissue. Ischemia leads to tissue damage because of lack of oxygen and nutrients and a build-up of metabolic wastes. Ischemia can also be caused by blockade or constriction of the blood vessels. Causes of tissue ischemia are atherosclerosis, embolism, hypotension, heart failure, thrombosis, sickle cell disease, diabetes, cerebrovascular accidents, and peripheral artery occlusive disease. The heart, the kidneys, and the brain are among the organs that are the most sensitive to ischemia. Ischemia of the brain causes a process called the "ischemic cascade" to be unleashed, in which proteolytic enzymes, and reactive oxygen species, damage neurons. Infarction is the process of tissue death (necrosis) caused by ischemia. Infarctions of heart and brain are commonly associated with hypertension, thrombosis or atherosclerosis. Peripheral vascular disease or peripheral artery occlusive disease includes many types of diseases caused by the obstruction of large arteries in the arms and legs. It can result from atherosclerosis, inflammatory processes leading to stenosis, or thrombus formation. It causes either acute or chronic ischemia (lack of blood supply), typically of the legs. Among the major causes of peripheral vascular diseases are smoking, diabetes, dyslipidemia and atherosclerosis, hypertension. Surgical treatments include angioplasty on solitary lesions in large arteries, plaque excision, in which the plaque is scraped off of the inside of the vessel wall; bypass grafting, sympathectomy—removing the sympatic ganglions leading to vasodilatation. At late stages with gangrene of toes, amputation is often required to prevent septicemia.

HSCs and HPCs of the current invention may be used for the purpose of treatment of ischemic lesions in peripheral artery occlusive diseases due to their ability to facilitate formation of vessels and enhance regeneration of tissue by stimulating cell proliferation as illustrated in detail in Example 6. Introduction of HSCs and HPCs of the current invention at the dose $5-50 \times 10^6$ cells at the site of ischemic lesions in peripheral artery occlusive diseases results in enhanced rate of new capillaries formation and enlargement of existing arteries, as illustrated in details in Example 6. This restoration occurs due to a massive and balanced release by the cells of current invention of multiple growth factors, like HGF, FGF, KGF, VEGF, GM-CSF.

Senescence (biological aging) is the transformation of the structure and function of an organism as it ages after its maturity. Senescence is not the predictable fate for all cells or organisms. A variety of cells and organisms have insignificant senescence. The process of aging is complex, and depends on a variety of different mechanisms and causes. Senescence is not universal, and cellular senescence evolved in certain species because it prevents the onset of cancer. Lifespans can vary significantly within and between species. Genetic and environmental factors contribute to aging process. Senescence is seen as a progressive failure of homeostasis involving genes for the maintenance and repair, stochastic events leading to molecular damage and molecular heterogeneity. Epigenetic factors play an important role in gene expression and aging as well as genetic factors. The role of telomeres in cellular senescence has been shown in some cells. The successive shortening of the chromosomal telomeres with each cell cycle limits the number of divisions of the cell, thus contributing to aging. The length of the telomere strand has senescence effects, telomere shortening activate extensive alterations in alternative RNA splicing that produce senescence toxins such as progerin. Many immortalized mammalian cell lines and tumors maintain or increase the overall length of their telomeres in the absence of telomerase activity by mechanisms as alternative lengthening of telomeres. In addition, damage to long-lived biopolymers, such DNA, could be caused by ubiquitous chemical agents in the body such as oxygen and sugars, are, therefore, part responsible for aging. The damage can include breakage of biopolymer chains, cross-linking of biopolymers, oxidative modifications. Free radicals can damage proteins, lipids or DNA. Chemical damage to structural proteins can leads to malfunction.

HSCs and HPCs of the current invention may be used for the purpose of reducing the rate or treatment of consequences of aging in organs or in the whole body due to their ability to produce hormones, cytokines and growth factors, which affect the aging process and stimulate cell proliferation as illustrated in detail in Example 7. Introduction of HSCs and HPCs of the current invention at the dose 5-500×10$^6$ cells as a singe dose or as a multiple courses of treatment which can be carried out for many years. HSCs and HPCs of the current invention by long-term engraftment, or independently of engraftment, produce multiple cytokines and growth factors, which influence genetic and epigenetic mechanisms responsible for cell, organ or organisms senescence. Therefore, HSCs and HPCs of the current invention slow down the aging process as their products influence the mechanisms of telomere lengthening, expression of genes involved in senescence process, induce up-regulation of antioxidant defense systems of cells and restore integrity of DNA and protein polymers.

EXAMPLES

Method to Augment Collection of HSCs and HPCs from Placenta

Example 1

HSCs and HPCs of the current invention were collected from 30 human term placentas by use of different cell-liberating compounds. Following IRB approval and informed consent, human term placentas were obtained from healthy females following caesarian section. Freshly obtained human placentas, which had been subjected to a conventional cord blood recovery process by draining substantially all of the cord blood from the placenta were used. Cord blood was collected from umbilical cord using standard techniques. Placentas were first infused with an anticoagulant/vasodilator solution (Heparin 30 U/ml, papaverin 0.05 mg/ml) at a temperature of 20° C. For infusion procedures, artery and vein of umbilical cord were further cannulated and connected to a reservoir. Pressure in the umbilical cord artery and vein was constantly measured using Baxter pressure transducers (Protocol Systems, Portland, Oreg.). Constant temperature of infusate was maintained using heat exchange unit connected to temperature-controlled water bath. Placentas was infused with 100 ml phosphate buffered saline with additives: heparin (10 U/ml); Papaverin (0.05 mg/ml); N-acetyl-cysteine (1 mM), gentamycin (0.05 mg/ml) (PBS+) (Experiment 1), or 100 ml PBS+ with 3 mg/L AMD3100 (Sigma, St. Louis, Mo.) (Experiment 2); or 100 ml PBS+ with 1 mg/ml BIO5192 (Experiment 3). BIO5192 was supplied by AnorMED (Vancouver, BC) as a sterile powder and reconstituted in pH 7.0 ethanol:propylene glycol:water (10:36:54). In Experiment 4 100 ml PBS+ with 1 mg/ml Trypsin and 0.1 mg/ml Collagenase I (Sigma, St. Louis, Mo.) was infused into the placental artery or vein. In Experiment 5 100 ml PBS+ with Etoposide (1 mM) was infused into placental vein. Placenta was then incubated for 3-8 hours at 37° C. in air.

Following incubation, fluid with cells was drained out of placental vessels and umbilical vein was infused with 100 ml of PBS and later flushed out 4 times via the umbilical artery. Collected cell suspension was centrifuged for 10 min at 1000 rpm, cells at the bottom collected and reconstituted in 10 ml PBS with heparin for further analyses.

The following analyses were performed on cord blood and cell suspensions obtained from placenta: number of total nucleated cells determined by flow cytometry, number of CD34$^+$ and CD34$^+$CD45$^{dim}$ cells determined by immunostaining with antibodies to CD34 and CD45, flow cytometry performed using FACS Calibur flow cytometer (BD Biosciences) and FlowJo software. Amounts of colony-forming unit cells were determined by culturing cells for 12-14 days in Methocult® medium (Stem Cell Technologies, Vancouver, Canada) according to manufacturer's instruction.

Results are shown in Table 1. Data obtained from cells collected from placental circulation were normalized to same variables obtained by analyses of cord blood cells (cord blood unit) collected from the corresponding placenta and are presented as percent of cord blood unit. As seen from Table 1, infusion of placental circulation with PBS did not yield substantial o CD34$^+$CD45$^{dim}$ or colony-forming unit cells. On the contrary, the described here novel method of using either CXCR4 inhibitor AMD3100 or integrin blocker BIO5192 for liberating HSCs, HPCs, colony-forming unit cells by infusion into chorionic circulation, resulted in very high yield of HPS and colony-forming unit cells

TABLE 1

Yield of TNC, CD34$^+$CD45$^{dim}$ cells and colony-forming unit cells (CFU) obtained from placenta and related to cord blood unit from the same donor. Mean data is given (%), N = 5. (*P < 0.05 compared to 1).

| | TNC | CD34$^+$CD45$^{dim}$ dim cells | CFU |
|---|---|---|---|
| 1. Infusion of PBS+ w/o cell-liberating composition | 23 | 14 | 18 |
| 2. AMD3100 | 31 | 412* | 332* |
| 3. BIO5192 | 24 | 524* | 423* |
| 4. Trypsin/Collagenase | 12 | 212* | 245* |
| 5. Etoposide | 18 | 185* | 211* |

Example 2

Same experimental setup was used as described for Example 1. Placentas were infused with PBS+ (Experiment 1), placed in PBS-filled bath and subjected either to ultrasound field (1 MHz, 2 W/m2) for 1 hour (Experiment 2), or to intermittent electromagnetic field 0.5 gauss for 1 hour total. Results in similar format as for Example 2 are shown in Table 2. Both ultrasound and electromagnetic field increased the amount of HCSs and HPCs obtained from placental circulation.

TABLE 2

Yield of TNC, CD34+CD45$^{dim}$ cells and colony-forming unit cells (CFU) obtained from placenta and related to cord blood unit from the same donor. Mean data is given (%), N = 5. (*P < 0.05 compared to 1).

|   | TNC | CD34+CD45$^{dim}$ cells | CFU |
| --- | --- | --- | --- |
| 1. Unfusion of PBS+ | 24 | 15 | 16 |
| 2. Ultrasound | 21 | 210* | 245* |
| 3. Electromagnetic field | 34 | 302* | 233* |

Example 3

Experiments were done in similar format as described for Example 1 and Example 2. Placentas were infused either with PBS+, PBS+ with AMD 3100 (3 mg/L), or PBS+ and BIO5192 (1 mg/ml), incubated for 8 hours and intermittently subjected to ultrasound filed at 1 MHz for 2 hours total. Results are shown in Table 3.

TABLE 3

Yield of TNC, CD34+CD45$^{dim}$ cells and colony-forming unit cells obtained from placenta and related to cord blood unit from the same donor. Mean data is given (%), N = 5. (*P < 0.05 compared to 1).

|   | TNC | CD34+ CD45 dim cells | CFU |
| --- | --- | --- | --- |
| 1. Infusion of PBS+ | 23 | 14 | 18 |
| 2. AMD3100 + Utrasound | 45 | 456* | 520* |
| 3. BIO5192 + Ultrasound | 38 | 568* | 563* |
| 4. PBS+ + Utlrasound | 32 | 324* | 231* |

The obtained results indicate, that infusion of placental vessels with composition containing cell liberating compounds followed by incubation with this composition, as well as treatment of placentas with ultrasound and electromagnetic fields allows to increase yield of HSCs, HPSs, and colony-forming unit cells as compared to corresponding cord blood unit collected from same donor.

To characterize cells collected by the method of the current invention in more detail and compare their properties to HSCs of cord blood a more detailed analyses of phenotype, colony-forming abilities and engraftment in mice was done. The Procount Progenitor Cell Enumeration Kit (BD Biosciences) containing fluorochrome-conjugated monoclonal antibodies directed against CD34 and CD45, in combination with the viability stain ToPro-3 iodide (Molecular Probes, Eugene, Oreg.), was used to determine live CD34+CD45$^{dim}$ cells in cord blood, tissue digests and placental perfusate using a FACSCalibur flow cytometer (BD Biosciences) and FlowJo analysis software (Tree Star, Inc., Ashland, Oreg.). Antibodies against KDR (R&D Systems, Cat# MAB3571) and CD31 (AbCam, Cat# ab59251) and CD133 (AbCam, Cat# ab16518) were used to identify cells in this population positive for these endothelial markers. In addition, fluorochrome-conjugated monoclonal antibodies directed against CD3 (PE-conjugated, Miltenyi Biotec, Cat#130-091-374), CD25 (PEconjugated, Miltenyi Biotec, Cat#120-001-311), CD45 (APC-conjugated, Caltag Laboratories, Cat# MHCD4505), CD51/61 (BD Pharmingen, Cat#550037) and CD235 (Dako, Denmark, Cat# R7078) were used to characterize cells in cell culture of mouse tissue. The ability to form blood cell-forming colonies in cell culture is an essential characteristic of the potential of CD34b /CD45dim cells to be used in transplant. Standard colony-forming analyses in MethoCultt medium to evaluate the viability and ability of placental-derived cells to differentiate was done. The placental cells generated a large number of colonies, including CFU-E (colony forming unit erythroid), BFU-E (burst-forming unit erythroid), CFU-GM (colony forming unit-granulocyte, macrophage), CFU-GEMM (colony forming unit-granulocyte, erythroid, macrophage, megakaryocyte).

Colonies generated from placenta HSCs obtained by the method of the current invention and cord blood showed a similar microscopic appearance and expressed hemoglobin.

Following a 2-week culture in Methocult medium, cells obtained from placenta were further characterized by flow cytometry and showed the presence of myeloid and erythroid lineages. Cells were isolated from culture medium and stained for human CD45 (pan leukocyte marker), CD25 (lymphocyte/monocyte marker), CD51/CD61 (megakaryocyte/platelet marker), and CD235 (human glycophorin A). Double staining for human CD45 and CD25, CD45 and CD51/CD61, for CD235 indicated presence of both lymphoid and erythroid lineages in cells obtained from placenta and from cord blood. There were no differences in colony-forming unit capacity, expression of lymphoid, myeloid and erythroid markers by HSCs obtained from placenta by the methods of current invention and cord blood from same placentas. Together these data indicate that cells from placental tissue differentiated into all hematopoietic lineages in vitro similarly as do cord blood cells. To study engraftment of HSCs of the current invention in animals, NOD/SCID mice (The Jackson Laboratory, Bar Harbor, Me.) were irradiated (2.5 Gy), and were injected IV with 1 million nucleated cells prepared from cord blood or from placenta by the methods of the current invention. After 3 months and weekly IP injection with erythropoietin (1 U), IL-3 (5 ng), stem cell factor (25 ng) and GM-CSF (5 ng) IP, the animals were sacrificed, and blood, bone marrow, and spleen cells were immunostained for human CD45 (pan-leukocyte), CD3 (lymphocyte), CD25 (lymphocyte/monocyte), and CD51-CD61 (platelet). Microscopic analysis of murine spleens 80 days post-injection showed cells positive for human CD45 and human HLA-DR in both groups. Mouse blood, bone marrow and spleen were further analyzed by flow cytometry for the presence of human cells. Flow cytometric analysis indicated the presence of human cells in blood and bone marrow that express human CD45. Blood, bone marrow and spleen were double-positive for CD45/CD3, CD45/CD25, and CD45/CD51/CD61 cells. Thus, NOD/SCID mice demonstrated chimerism for human blood cells following transplantation of placenta-derived HSCs similar as for transplantation with cord blood.

As is shown by Examples 1-3, collected HSCs from placenta by the method of this invention show phenotype (CD34+CD45$^{dim}$) and properties to form colonies of erythrocytes, leukocytes and megacaryocytes in culture, as well as repopulate immunodeficient mice as human blood lineages which are indistinguishable from HSCs of cord blood. This evidence indicates that placental HSCs obtained by the method of the current invention could be used in humans in the same fashion as cord blood cells for the treatment of blood disorders in various conditions.

Example 4

Treatment of Acute Inflammatory Diseases

Therapeutic use of HSCs of the current invention for the treatment of bacterial sepsis.

Cells obtained from human placentas, treated with AMD 3100 as described above in Example 1 (HSCs), were used for this study. In animal model of injury, C57BL/6 male mice (8-10 wk old; Jackson Laboratories, Bar Harbor, Me.) were used. Sepsis (SIRS) was induced by the IP administration of live $E.\ coli$ JM109 at a dose $5 \times 10^7$ cfu/animal. Mice were then allowed to recover. Then, 4 hours after the induction of sepsis, mice were given either human HPS (0.5 $10^6$ cells in 100 µl of PBS) or same amounts cultured human fetal fibroblasts as negative control IV. Survival in each group was noted. At the end of either 24, 48, 72, or 120 hours, samples were collected from sample mice for assessment of liver, lung injury, biochemical analysis, cytokine analyses and histology.

In S/D rats 250 g weight sepsis was induced by caecal ligation and puncture. Under general anesthesia abdomen was opened, caecum isolated and ligated with caecal artery so that 25 mm of distal caecum was left without circulation. Six hours later, rats were given either HSCs ($5 \times 10^6$ cells in 100 µl of PBS) or same amounts cultured human fetal fibroblasts as negative control IV. Survival in each group was noted.

The time course of animal death is shown in Table 4.1 for mice and in Table 4.2 for rats. In both groups, at time points after 48 hours there was significant improvement in survival rate of animals, who received treatment with HSCs.

Cytokine profile in plasma was measured at 12 and 24 hours in peripheral blood of mice by LincoPlex® immunoassays kit, which allowed measurements of up to 24 different cytokines and growth factors. Cytokines measured in plasma MIP-1α; GM-CSF; MCP-1; KC; RANTES; INF-γ; IL-1α; IL-1β; G-CSF; IP-10; IL-2; IL-4; IL-5, IL-6, IL-7, IL-10; IL-12p70, TNF-α; IL-9; IL-13; IL-15; IL-17. Results are illustrated in Table 4.3 for those cytokines and growth factors, which demonstrated significant difference. In general, a clear trend was observed towards decrease of some pro-inflammatory cytokines (TNF-α, MIP-1), while others (MIP-1, IL-1) were significantly increased. Very significant changes were observed in multi-fold increase in anti-inflammatory cytokines IL-10 and IL-13. Taken together, these results indicated that therapy with HSCs from placenta significantly shifted balance of pro- and anti-inflammatory cytokines in the body during bacterial sepsis and thus significantly reduced mortality.

In an additional group of mice at 48 hours, survivors of both groups were sacrificed and autopsy was performed. In control group treated with fibroblasts, the following pathological findings were observed: ischemic encephalopathy, myocardial necrosis, focal coagulation necrosis, subendocardial hemorrhage. Intensive tubular necrosis was evident in kidneys. Lungs were edematous with massive leukocyte infiltration and multiple thrombosis and diffuse alveolar damage. Liver developed fatty changes and hemorrhagic necrosis. In animals treated with infusion of HSCs, these pathologic changes were minimal. This example demonstrates that using of placental cells and their products in bacterial sepsis as a treatment prevents death and multi-organ damage.

TABLE 4.1

Effect of placental HSCs on survival in mice administered $E.\ coli$. (*$P < 0.05$ compared to fibroblasts).

|  | Survival At 24 h, % | Survival At 48 h, % | Survival At 72 h, % | Survival At 120 h, % |
|---|---|---|---|---|
| Fibroblasts | 60 | 45 | 35 | 5 |
| HSCs | 100 | 85 | 75* | 55* |
| Carrier (medium) | 70 | 40 | 30 | 20 |

TABLE 4.2

Effect of placental HSCs on survival in rats following caecal ligation and puncture. (*$P < 0.05$ compared to fibroblasts).

|  | Survival At 24 h, % | Survival At 48 h, % | Survival At 72 h, % | Survival At 120 h, % |
|---|---|---|---|---|
| Fibroblasts | 85 | 65 | 45 | 30 |
| HSCs | 90 | 85 | 80* | 75* |
| Carrier (medium) | 80 | 70 | 40 | 10 |

TABLE 4.3

Cytokine profile in plasma of mice subjected to bacterial sepsis. Effect of treatment with HSCs of the current invention. Significant changes (by ANOVA) or trends were found only for cytokines, given in Table below, for other cytokines no changes or trends were present (*$P < 0.05$ compared to fibroblasts).

| Plasma 8 h | IL-10 pg/ml | TNF-α pg/ml | IL-13 pg/ml |
|---|---|---|---|
| Control Fibroblasts | 785 ± 100 | 130 ± 30 | 60 ± 10 |
| HSCs | 2800 ± 400* | 50 ± 10 | 220 ± 38 |
| Carrier | 200 ± 50* | 150 ± 24* | 60 ± 10* |

Example 5

Therapeutic Use of HSCs of the Current Invention for the Enhancement of Bone Fracture Regeneration To test effect of placenta-derived cells on healing of closed bone fractures of tibia, experiments were performed in rabbits. The animals were anesthetized before inflicting a closed fracture, and antero-posterior radiographs were taken. Four groups of animals received injection of $10^7$ cells to the site of bone fracture 48 hours following fracture. Human fibroblasts were used as controls, and HSC obtained o placenta were tested. Closed bone fractures were first produced in skeletally mature, female, New Zealand White Rabbits. Then ten rabbits from each group were euthanized at either two or four weeks of recovery. Bone specimens were taken for biomechanical evaluation and for histology. Histological specimens in each group were decalcified, embedded in celloidin, and stained with hematoxylin and eosin. Each of the sections was given a bridging score between 0 and 6. The maximum histologic score of 6 indicated that both the medial and lateral sides at the callus were bridged in all sections. Results are shown in Table 5. Placental stem cell lines increased the rate of bone regeneration significantly.

TABLE 5

Cells of human placenta significantly increased
the rate of bone regeneration following bone fracture.
(*P < 0.05 compared to fibroblasts).

|  | Histological score 2 weeks | Histological score 4 weeks |
|---|---|---|
| Fibroblasts | 2.2 ± 0.5 | 3.2 ± 0.6 |
| HSCs | 4.5 ± 0.5 | 5.8 ± 0.2* |

Example 6

Therapeutic Use of HSCs of the Current Invention for Enhancement of Perfusion Abnormalities Following Peripheral Artery Occlusions This example is to demonstrate that HSCs from placenta are capable of decreasing perfusion-induced abnormalities after femoral artery occlusion following systemic administration. 30 rabbits were used to investigate effect of HSCs from placenta on recovery of following femoral artery occlusion. To model the femoral artery occlusion, anesthetized rabbits were intubated, ventilated and femoral artery of one leg was isolated and ligated. Following femoral artery occlusion, $5 \times 10^6$ fibroblasts (n=10) or $5 \times 10^6$ HSCs (n=10) were delivered intravenously. Ten animals received sham operation. Animals were allowed to recover for 6 months. Perfusion of m.quadriceps femoris was assessed by injection of $^{131}$I-labeled microspheres. Following injection, animals were euthanized, m.quadriceps femoris in the region of infarction as well as control regions of the contralateral leg was used to determine the specific activity of microspheres present in tissue. Perfusion was expressed as percentage of specific activity present in m.quadriceps femoris of the contralateral leg. M.quadriceps femoris was also used for histological examination of the number of vessels per surface unit area and stained for collagen (Mason TriChrome Stain). The results are shown in Table 6. Histological examination demonstrated presence of fibrotic changes in the m.quadriceps femoris of the operated leg, treated by fibroblast injection. Tricrome staining demonstrated large amounts of collagen in these areas. These pathological changes were absent or minimal in animals, injected with CCFUC.

Example 7

HSCs Reduce the Rate of Aging and DNA Damage.

HSCs and HPCs of the current invention were tested in vitro culture for their capability to reduce aging process and related DNA and protein oxidative damage. Several tests were used to determine influence of HSCs of current invention on the following processes: 1. Assessment of proliferation rate and proliferation limit in human fibroblasts; 2 Assessment of DNA oxidative damage by DNA oxidation and formation of DNA double-strand breaks; 3. Assessment of protein oxidation. These variables were measured in co-cultures of human fibroblasts and HSCs of the current invention. Human fibroblasts were cultured in DMEM/F12 media with 10% fetal calf serum. Cells were passaged every 5 days. Fibroblasts were co-cultured with HSCs in 3 micron-pore Costar inserts without direct contact between two cells for 1 day in proliferation assay analyses, and for 2 hours in cultures following oxidative stress. Oxidative stress was induced by Menadione (for 8-oxoG), by etoposide (for DNA double-strand breaks and by hydrogen peroxide (1 mM) for proteiun oxidation.

DNA oxidation analysis is based on the fact that avidin binds with high affinity to 8-oxoG in DNA. Here we used fluorescein isothiocyanate (FITC)-avidin (Sigma) and flow cytometry (Beckton-Dickinson, Franklin Lakes, N.J., USA; FACS Calibur) for detection of 8-oxoG. Cells were treated with the oxidative agent menadione (Sigma) in serum-free and phenol red-free DMEM (Invitrogen), detached from the plastic with trypsin EDTA, washed in NaCl, and fixed in 2% formaldehyde at 4° C. and then in 80% ethanol at 20° C. Other steps before FACS analysis were performed as described in the instructions to the OxyDNA fluorimetric kit (catalogue no. 500095) produced by Calbiochem (San Diego, Calif., USA). FITC-avidin binding was quantified by relative peak shift (M1 gate) in the FACS histograms obtained. Double strand DNA breaks were determined by immunostaining for phosphorylated histone H2AX. Protein oxidation in some cell cultures was done by immunohistochemical analyses. Analyses for oxidized proteins were performed by measurements of carbonyl groups after derivatization with dinitrophenylhydrazine (DNPH) and staining with anti-DNPH antibody (Sigma-Eldrich, St. Louis, Mo.). Cells were grown on the glass coverslips, fixed in ethanol, and derivitized by DNPH. After double washing, immunostaining and laser confocal microscopy were done. Results are summarized in Table 7.

TABLE 6

Human placental HSCs enhance perfusion and relative capillary density following femoral artery occlusions.

| Group | Control Experimental leg | Control Contra-lateral leg | HSCs Experimental Leg | HSCs Contra-lateral Leg | Fibroblasts Experimental leg | Fibroblasts Contra-lateral leg |
|---|---|---|---|---|---|---|
| Perfusion | 0.3 ± 0.2 | 0.9 ± 0.15 | 0.6 ± 0.1* | 0.9 ± 0.1 | 0.4 ± 0.2 | 1.2 ± 0.2 |
| Relative capillary Density | 0.2 ± 0.1 | 0.9 ± 0.18 | 0.7 ± 0.1* | 0.9 ± 0.1 | 0.3 ± 0.1 | 1.1 ± 0.2 |

(*P < 0.05 compared to control).

TABLE 7

Proliferation characteristics and indexes of DNA and cell protein oxidation in oxidative challenges as a function of human fibroblast co-cultures with HSCs. (*P < 0.05).

| Group | Fibroblast Doubling Time | Number of passages before senescence | Oxydized DNA (% cells) | DNA double-strand breaks by histone H2AX phosphorylation (% cells) | Protein oxidation (% cells) |
|---|---|---|---|---|---|
| Fibroblasts | 45 ± 3 | 12 ± 2 | 32 ± 2 | 12 ± 2 | 35 ± 4 |
| Fibroblasts Co-cultured with HSCs | 34 ± 2* | 25 ± 3* | 17 ± 3* | 5 ± 1* | 12 ± 2* |

The given results indicate, that co-culture of human fibroblasts with HSCs of current invention significantly increases cell proliferation, limit for senescence, while significantly decreasing DNA and protein oxidative damage in cells. Therefore, in accepted models of human cell senescence and senescence—related DNA and protein damage, introduced HSCs have a potential to reduce aging and aging-associated cell damage.

The invention claimed is:

1. A method of obtaining hematopoietic stem cells from a placenta, comprising the steps of:
   a. infusing placental tissue with a composition comprising a cell preservation compound to provide infused placental tissue without simultaneous effusion;
   b. incubating said infused placental tissue for a duration to provide incubated placental tissue that releases hematopoietic stem cells, wherein said duration is selected from the group consisting of:
      i. about 2 hours to about 3 hours;
      ii. about 3 hours to about 4 hours;
      iii. about 4 hours to about 6 hours;
      iv. about 6 hours to about 8 hours; and
      v. about 8 hours to about 12 hours; and
   c. isolating hematopoietic stems cells from the incubated placental tissue; wherein the infused placental tissue or incubated placental tissue is exposed to at least one of ultrasonic radiation or an electromagnetic field.

2. The method of claim 1, wherein the method comprises exposing the infused placental tissue or incubated placental tissue to ultrasonic radiation.

3. The method of claim 1, wherein the method comprises exposing the infused placental tissue or incubated placental tissue to an electromagnetic field.

4. The method of claim 3, wherein the electromagnetic field has a strength of at least 0.5 gauss.

5. The method of claim 1, wherein said incubating is performed at a temperature of about 20° C. for at least 2 hours.

6. The method of claim 1, wherein said isolating comprises (i) eluting a suspension of cells from the incubated placental tissue to provide a cellular suspension, and (ii) subjecting the cellular suspension to centrifugal separation and thereafter harvesting hematopoietic stem cells.

7. The method of claim 1, wherein said composition further comprises at least one cell adhesion receptor blocker.

8. The method of claim 1, wherein the cell preservation compound is an antioxidant.

9. The method of claim 7, wherein the cell adhesion receptor blocker is a CXCR4 receptor antagonist, an integrin inhibitor, a biocompatible non-ionic detergent, a PCAM receptor antagonist, a PCAM receptor antibody, an ICAM-blocking compound, a VCAM-blocking compound, a CD56 (NCAM)-blocking compound, a proteolytic enzyme, a fibronectin receptor-blocking compound, or a calcium chelator.

10. The method of claim 7, wherein the cell adhesion receptor blocker is etoposide.

11. The method of claim 1, wherein the hematopoietic stem cells have phenotype $CD34^+CD45^{dim}$.

12. A method of obtaining hematopoietic stem cells from a placenta, comprising the steps of:
   a. infusing a placenta or placental tissue with a cell-liberating composition comprising a cell preservation compound without simultaneous effusion, and then intermittently exposing the placenta or placental tissue to ultrasonic radiation while incubating the placenta or placental tissue for a duration ranging from 3 hours to 8 hours to provide incubated placental tissue that releases hematopoietic stem cells; and
   b. isolating hematopoietic stems cells from the incubated placental tissue.

13. The method of claim 1, wherein said incubating is performed for a period of time selected from the group consisting of:
   a. about 4 hours to about 6 hours;
   b. about 6 hours to about 8 hours; and
   c. about 8 hours to about 12 hours.

14. The method of claim 1, wherein said incubating is performed for a period of time of about 8 hours to about 12 hours.

* * * * *